US011491311B2

(12) United States Patent
Selkee

(10) Patent No.: US 11,491,311 B2
(45) Date of Patent: *Nov. 8, 2022

(54) SELF-HOLDING MEDICAL DEVICE CONTROL HANDLE WITH CAM ACTUATED CLUTCH MECHANISM

(71) Applicant: BIOSENSE WEBSTER (ISRAEL) LTD., Yokneam (IL)

(72) Inventor: Thomas V. Selkee, Claremont, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 746 days.

This patent is subject to a terminal disclaimer.

(21) Appl. No.: 16/415,207

(22) Filed: May 17, 2019

(65) Prior Publication Data
US 2019/0269887 A1 Sep. 5, 2019

Related U.S. Application Data

(63) Continuation of application No. 14/819,353, filed on Aug. 5, 2015, now Pat. No. 10,293,138, which is a (Continued)

(51) Int. Cl.
*A61M 25/01* (2006.01)
*A61B 18/00* (2006.01)
(Continued)

(52) U.S. Cl.
CPC ....... *A61M 25/0147* (2013.01); *A61B 1/0052* (2013.01); *A61B 5/283* (2021.01);
(Continued)

(58) Field of Classification Search
CPC .......... A61M 25/0147; A61M 25/0136; A61M 2025/015; A61B 1/0052; A61B 5/283;
(Continued)

(56) References Cited

U.S. PATENT DOCUMENTS

| 5,195,968 | A | 3/1993 | Lundquist et al. |
| RE34,502 | E | 1/1994 | Webster, Jr. |
| 5,628,775 | A * | 5/1997 | Jackson ............ A61M 25/0147 607/116 |
| 6,485,455 | B1 | 11/2002 | Thompson et al. |

(Continued)

FOREIGN PATENT DOCUMENTS

| CN | 102232869 A | 11/2011 |
| EP | 2172241 A2 | 4/2010 |

(Continued)

OTHER PUBLICATIONS

Extended European Search Report for European Application No. 12197175.8, dated Mar. 27, 2013, 5 pages.

*Primary Examiner* — Nathan R Price
*Assistant Examiner* — Anh Bui
(74) *Attorney, Agent, or Firm* — Etan S. Chatlynne; Calderon Safran & Cole, P.C.

(57) ABSTRACT

A medical device control handle has a first actuation assembly and a second actuation assembly, wherein each assembly has a shaft that is axially aligned but not rotationally coupled with the other shaft. The first actuation assembly includes a first actuation member and a clutch mechanism having a friction disk for generating frictional torque in rendering the first actuation member self-holding. The first actuation member has a cam portion adapted to impart translational motion and rotational motion for disengaging the clutch mechanism upon pivotation of the first actuation member, thus allowing rotation of the first shaft to manipulate a feature of the medical device, for example, deflection. The second actuation assembly includes a second actuation member and a translating member that is responsive to rotation of the second shaft so as to manipulate another feature of the medical device. The second actuation member is also self holding.

11 Claims, 12 Drawing Sheets

Related U.S. Application Data continuation of application No. 13/327,448, filed on Dec. 15, 2011, now Pat. No. 9,101,269.

(51) Int. Cl.

| | |
|---|---|
| *A61B 18/14* | (2006.01) |
| *A61B 5/283* | (2021.01) |
| *A61B 5/287* | (2021.01) |
| *A61B 1/005* | (2006.01) |
| *A61B 90/00* | (2016.01) |
| *A61B 5/00* | (2006.01) |

(52) U.S. Cl.
CPC .............. *A61B 5/287* (2021.01); *A61B 18/00* (2013.01); *A61B 18/1492* (2013.01); *A61M 25/0136* (2013.01); *A61B 5/6857* (2013.01); *A61B 2018/00351* (2013.01); *A61B 2018/00357* (2013.01); *A61B 2018/00577* (2013.01); *A61B 2018/00952* (2013.01); *A61B 2090/397* (2016.02); *A61B 2562/17* (2017.08); *A61M 2025/015* (2013.01)

(58) Field of Classification Search
CPC ....... A61B 5/287; A61B 5/6857; A61B 18/00; A61B 18/1492; A61B 2018/00577; A61B 2018/00952
See application file for complete search history.

(56) References Cited

U.S. PATENT DOCUMENTS

| | | | |
|---|---|---|---|
| 6,579,278 B1 | 6/2003 | Bencini | |
| 6,648,875 B2 | 11/2003 | Simpson et al. | |
| 7,377,906 B2 | 5/2008 | Selkee | |
| 9,101,269 B2* | 8/2015 | Selkee | A61B 5/287 |
| 10,293,138 B2* | 5/2019 | Selkee | A61B 18/00 |
| 2001/0034472 A1* | 10/2001 | Fujii | A61B 1/0052 |
| | | | 600/146 |
| 2002/0082584 A1 | 6/2002 | Rosenman et al. | |
| 2002/0161330 A1 | 10/2002 | Nguyen | |
| 2002/0165484 A1* | 11/2002 | Bowe | A61M 25/0136 |
| | | | 604/95.05 |
| 2005/0060016 A1* | 3/2005 | Wu | A61F 2/966 |
| | | | 623/1.11 |
| 2005/0272975 A1* | 12/2005 | McWeeney | A61B 6/06 |
| | | | 600/172 |
| 2005/0288656 A1 | 12/2005 | Koerner et al. | |
| 2006/0270976 A1 | 11/2006 | Savage et al. | |
| 2010/0004633 A1 | 1/2010 | Rothe et al. | |

FOREIGN PATENT DOCUMENTS

| | | |
|---|---|---|
| EP | 2289408 A1 | 3/2011 |
| EP | 2172241 B1 | 12/2012 |
| EP | 2532297 A1 | 12/2012 |
| JP | H06292728 A | 10/1994 |
| JP | 2007181689 A | 7/2007 |
| JP | 2011045719 A | 3/2011 |
| RU | 2033108 C1 | 4/1995 |
| WO | 2011136366 A1 | 11/2011 |

* cited by examiner

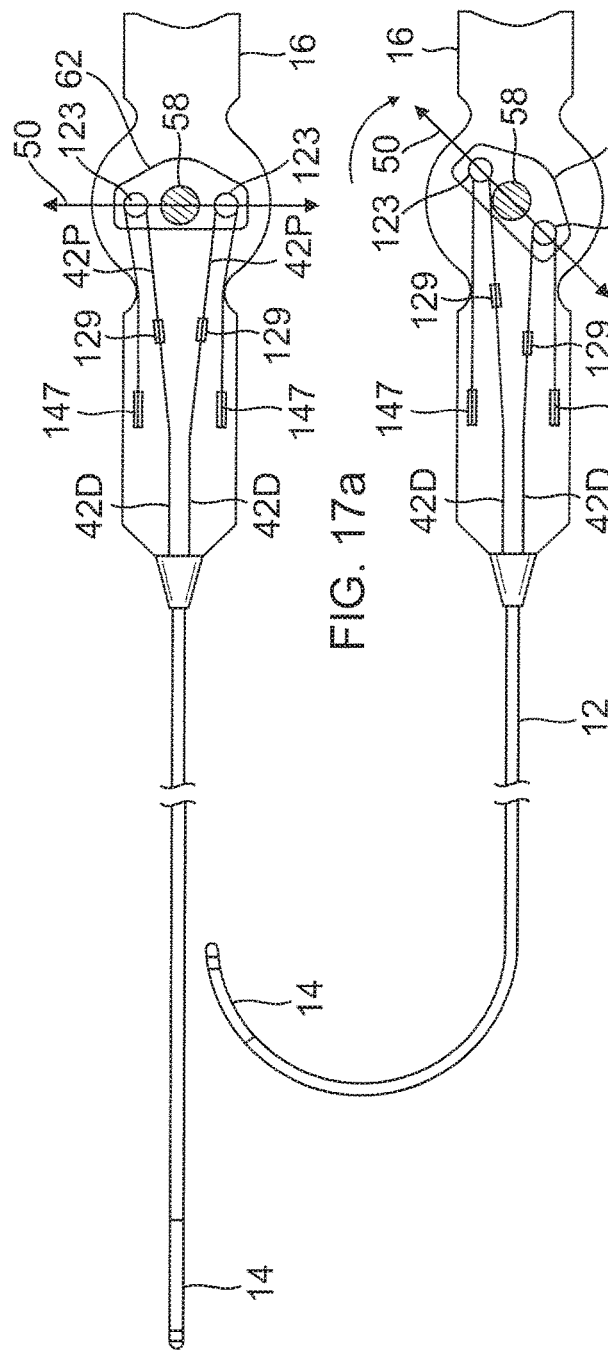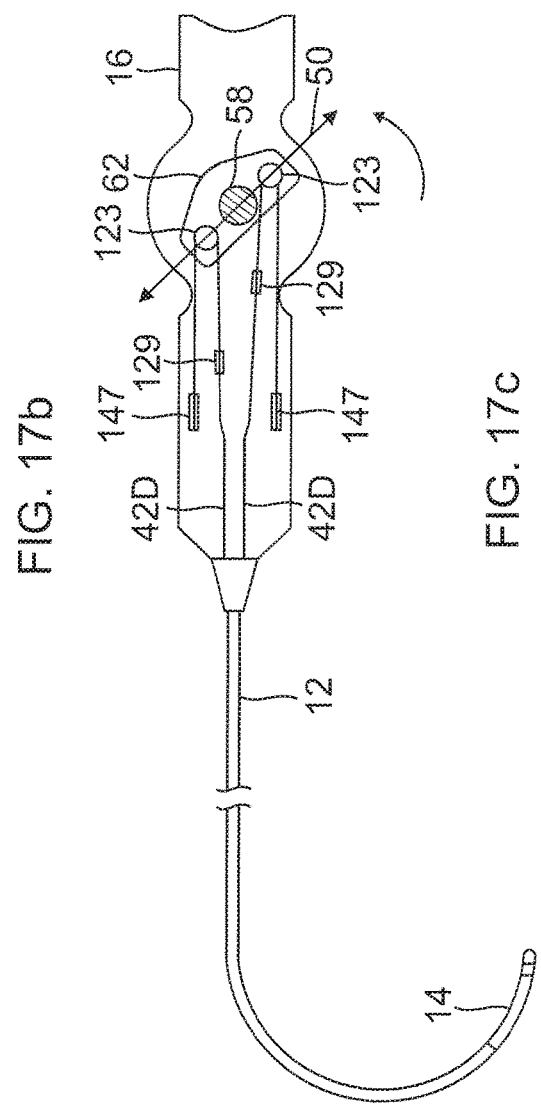

SELF-HOLDING MEDICAL DEVICE CONTROL HANDLE WITH CAM ACTUATED CLUTCH MECHANISM

CROSS-REFERENCE TO RELATED APPLICATION(S)

The present application is a Continuation under 35 U.S.C. § 120 of U.S. patent application Ser. No. 14/819,353, filed Aug. 5, 2015, which is a Continuation under 35 U.S.C. § 120 of U.S. patent application Ser. No. 13/327,448, filed Dec. 15, 2011, now U.S. Pat. No. 9,101,269. The entire contents these applications are incorporated by reference herein in their entirety.

FIELD OF INVENTION

This invention relates to a control handle for medical devices, in particular, a control handle having multiple mechanisms controlling multiple puller wires.

BACKGROUND

Electrode catheters have been in common use in medical practice for many years. They are used to stimulate and map electrical activity in the heart and to ablate sites of aberrant electrical activity. Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. Prior to treating the condition, one has to first determine the location of the wavelets. Various techniques have been proposed for making such a determination, including the use of catheters with a mapping assembly that is adapted to measure activity within a pulmonary vein, coronary sinus or other tubular structure about the inner circumference of the structure. One such mapping assembly has a tubular structure comprising a generally circular main region generally transverse and distal to the catheter body and having an outer circumference and a generally straight distal region distal to the main region. The tubular structure comprises a non-conductive cover over at least the main region of the mapping assembly. A support member having shape-memory is disposed within at least the main region of the mapping assembly. A plurality of electrode pairs, each comprising two ring electrodes, are carried by the generally circular main region of the mapping assembly.

In use, the electrode catheter is inserted into a guiding sheath which has been positioned a major vein or artery, e.g., femoral artery, and guided into a chamber of the heart. Within the chamber, the catheter is extended past a distal end of the guiding sheath to expose the mapping assembly. The catheter is maneuvered through movements that include deflection of a distal portion of the catheter so that the mapping assembly is positioned at the tubular region in the heart chamber. The ability to control the exact position and orientation of the catheter and also the configuration of the mapping assembly is critical and largely determines how useful the catheter is.

Steerable catheters are generally well-known. For example, U.S. Pat. No. Re 34,502 describes a catheter having a control handle comprising a housing having a piston chamber at its distal end. A piston is mounted in the piston chamber and is afforded lengthwise movement. The proximal end of the elongated catheter body is attached to the piston. A puller wire is attached to the housing and extends through the piston, through the catheter body, and into a tip section at the distal end of the catheter body. The distal end of the puller wire is anchored in the tip section of the catheter. In this arrangement, lengthwise movement of the piston relative to the housing results in deflection of the catheter tip section.

The design described in U.S. Pat. No. RE 34,502 is generally limited to a catheter having a single puller wire. If bi-directional deflection is desire, more than one puller wire becomes necessary. Moreover, if more control is desired, such as contraction of the mapping assembly, an additional puller wire is needed. Furthermore, it is desirable that the mechanisms for actuating the puller wires be self-holding such that the mechanisms can maintain deflection of the catheter and/or contraction of the mapping assembly without the need for continuous control by the user. Accordingly, a need exists for a control handle capable of moving multiple puller wires that can be used in a hands-free manner.

SUMMARY OF THE INVENTION

The present invention is directed to a medical device control handle. As medical devices, especially, electrophysiology catheters, become more complex with more components to actuate, a control handle should provide independent control of multiple puller members. The control handle of the present invention utilizes a first actuation assembly for actuating at least one puller member in manipulation of a feature of the medical device, and a second actuation assembly for actuating another puller member in manipulation of another feature of the medical device, wherein the first and second actuation assemblies define a common rotational axis without being rotationally coupled to each other.

In one embodiment, the first actuation assembly has a shaft, and a first actuator, a pulley arm, and a clutch mechanism, each mounted on and rotationally coupled to the shaft, wherein the pulley arm is adapted to act on at least one puller member. Mounted at or near an end of the shaft, the first actuator extends in a plane that is generally perpendicular to the shaft where it can be pivoted out of the plane and rotated by a user. The clutch mechanism includes a friction disk that is also mounted on the shaft and renders the first actuator self-holding by resisting rotation about the shaft through frictional contact with a friction-inducing surface inside the control handle. Advantageously, the shaft is adapted for translational movement which removes the friction disk from contact with the friction-inducing surface when the actuator is pivoted out of the plane for disengaging the clutch mechanism, and for rotational movement which actuates the puller member when the actuator is rotated. The at least one puller member extends from the control handle to a first feature of the medical device so that the user can adjust the first feature, e.g., deflection of an intermediate section, by manipulating the first actuator.

In a more detailed embodiment, the first actuator is an elongated knob having a cam portion with two cam surfaces, wherein one cam surface is adapted to disengage the clutch mechanism by translating the shaft in one direction to move the friction disk out of contact with the friction-inducing surface thereby allowing rotation of the shaft and pulley arm to actuate the puller member, and another cam surface is adapted to engage the clutch mechanism by translating the shaft in an opposite direction to move the friction disk back into contact with the friction-inducing surface thereby resisting rotation of the shaft. A compression loading washer is mounted on the shaft to preload the assembly so that the clutch mechanism remains engaged to render the first actuator self-holding until actively disengaged by the user.

In another embodiment, the control handle includes a second puller member and a second actuation assembly having a second shaft, a second actuator mounted on and rotationally coupled to the second shaft, and a translation member responsive to rotation of the second shaft, wherein a proximal end of the second puller member is anchored in the translation member for actuation when the second actuator is rotated by the user. In a more detailed embodiment, the second shaft has a spur gear formation which upon rotation acts on a rack formation on the translation member to move the translation member. A rotational axis of the second shaft is in axial alignment with the rotational axis of the first actuation assembly as a space saving measure but the two shafts are rotationally independent of each other. The second puller member extends from the control handle to a second feature in the medical device so that a user can adjust the second feature, e.g., a distal assembly having a helical portion, by manipulating the second actuator. The second actuator is also self-holding by means of a compression-loading washer mounted on the second shaft.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIGS. 17A-17C are schematic diagrams of an embodiment of a control handle in a neutral configuration, a right deflection configuration, and a left deflection configuration.

DETAILED DESCRIPTION OF THE INVENTION

Figure 1:
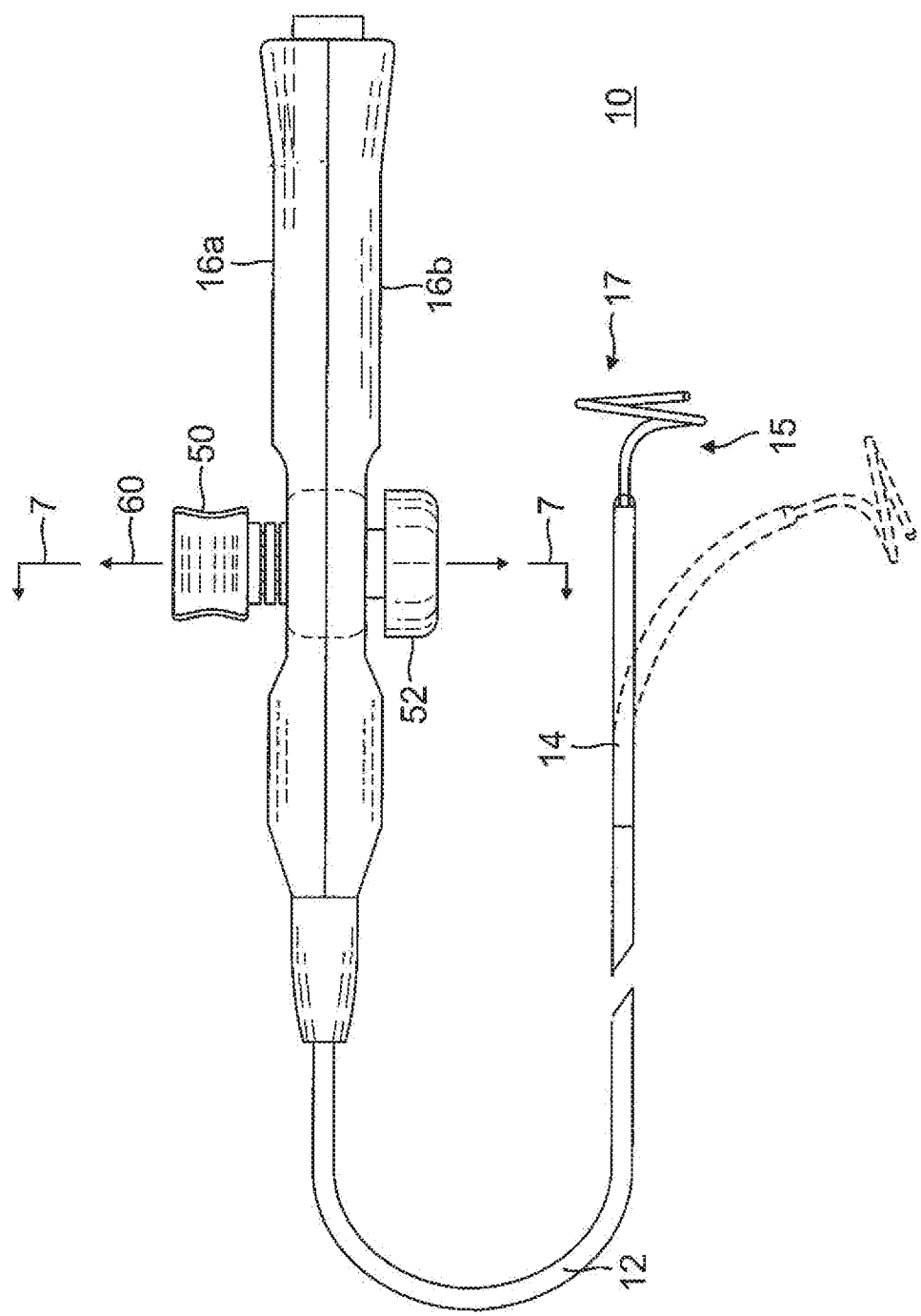
FIG. 1 is a top plan view of one embodiment of the catheter of the present invention.

The present invention is directed to a control handle 10 for use with a medical device with at least two tensile puller members, e.g., puller wires or the like, for actuating at least two independent movements or manipulations of components of the medical device. The control handle may be used with any variety of medical devices, for example, an electrophysiology (EP) catheter 10 configured for mapping and/or ablation of tissue, including the heart, an embodiment of which is illustrated in FIG. 1. Advantageously, a first actuator is used to manipulate a feature of the medical device and a second actuator is used to manipulate another feature of the medical device.

The catheter 10 of FIG. 1 comprises an elongated catheter body 12, a deflectable intermediate section 14 at a distal end of the catheter body 12, and a tip section 15 including a distal assembly 17 having, for example, a helical form, at a distal end of the intermediate section 14. In the illustrated embodiment of FIGS. 1 and 6, a control handle 16 for use with the catheter has a first actuator, e.g., bi-directional deflection knob 50, that is configured to actuate at least one puller wire, if not a pair of puller wires, extending from the control handle 16 and through the catheter body 12 and intermediate section 14 for uni- or bi-directional deflection of the intermediate section. In accordance with a feature of the present invention, the control handle has a second actuator, e.g., a dial 52, opposing the first actuator 50, for actuating yet another (or third) puller wire for independent manipulation or adjustment of a distal assembly 17 extending from the intermediate section 14, for example, to contract the helical form of the distal assembly. Each actuator can be operated separately and independently without affecting the other actuator or its puller wire(s).

Figure 2A:
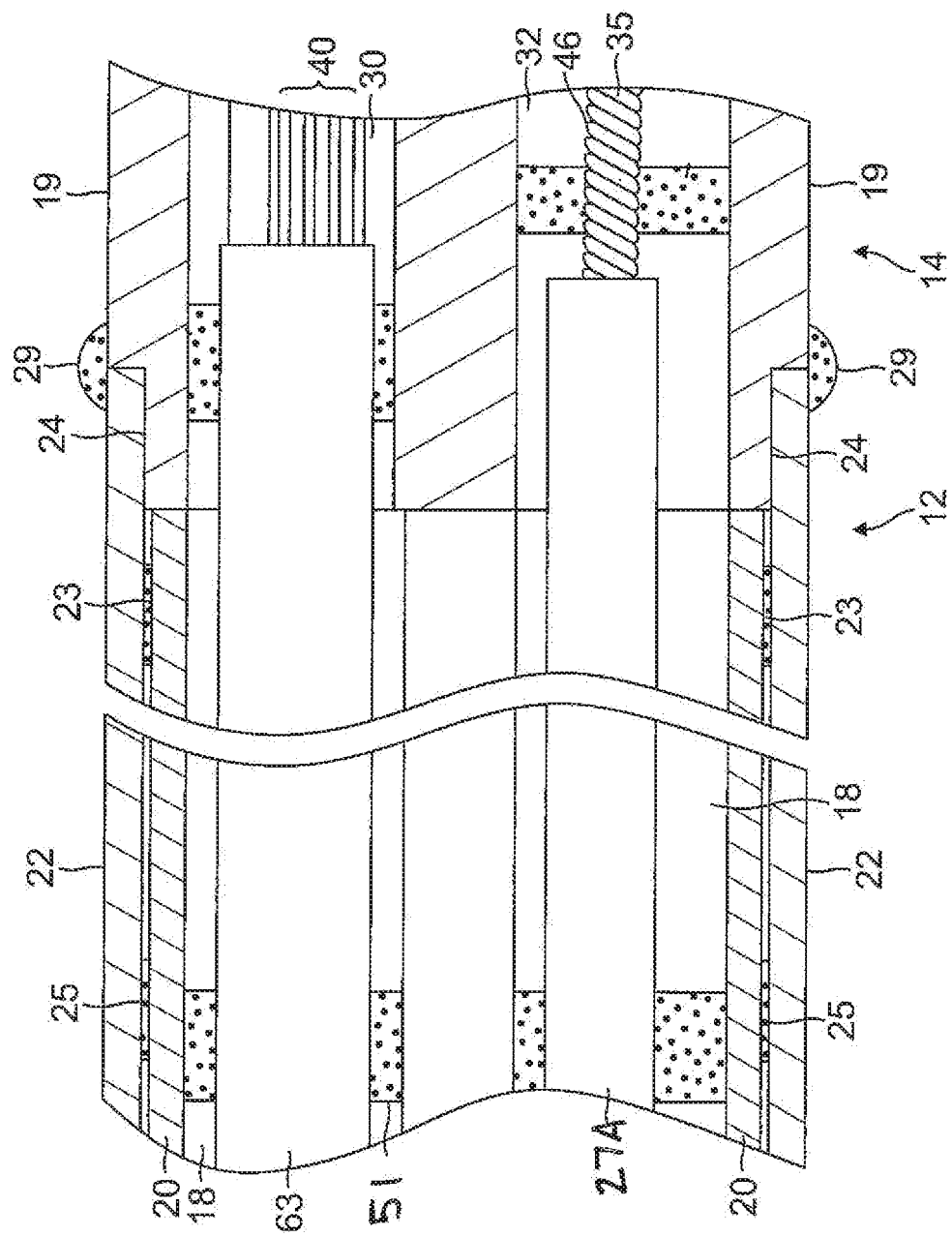
FIG. 2A is a side cross-sectional view of an embodiment of a junction of a catheter body and an intermediate section, taken along a first diameter.
Figure 2B:
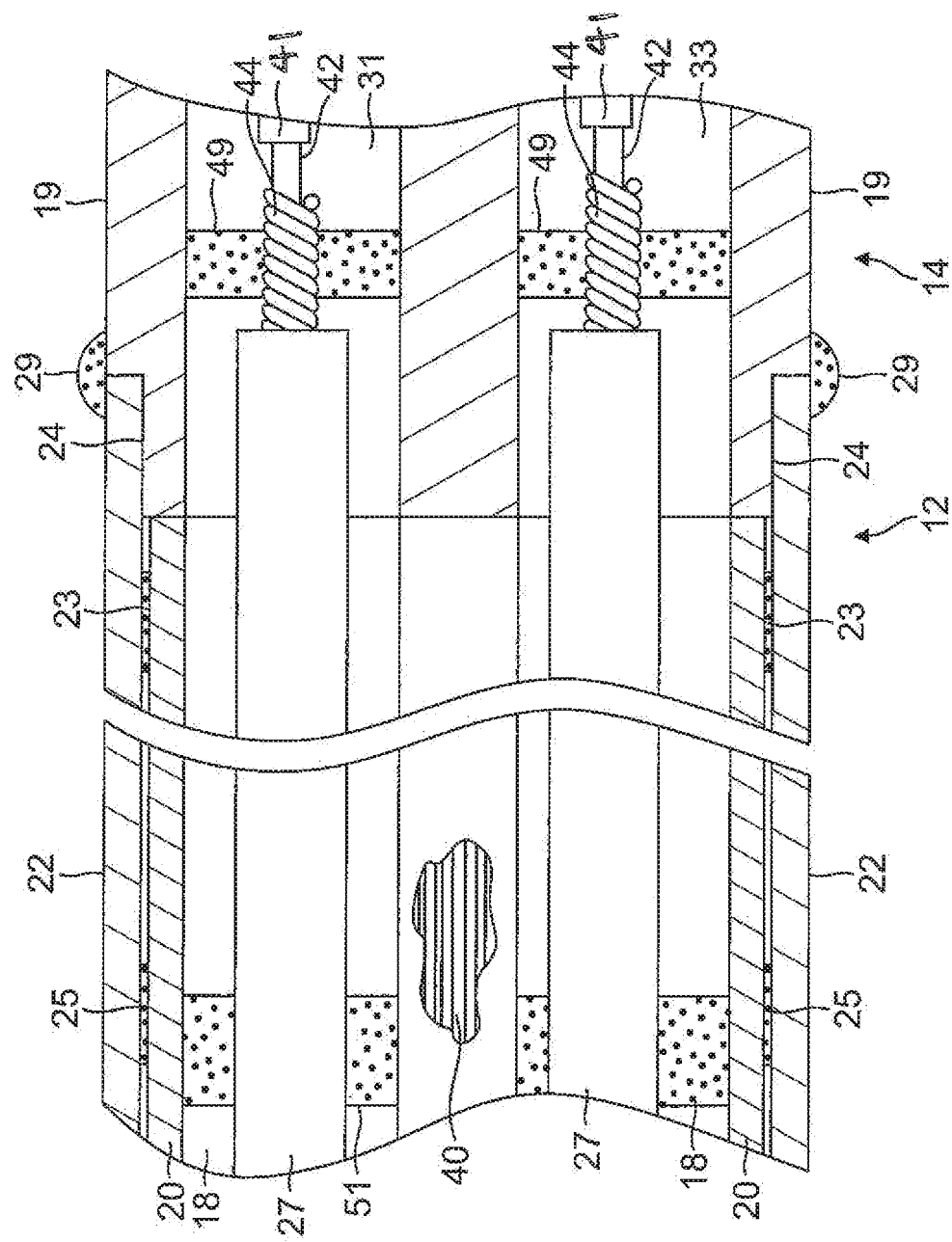
FIG. 2B is a side cross-sectional view of the embodiment of the junction of FIG. 2A, taken along a second diameter generally perpendicular to the first diameter.

With reference to FIGS. 2A and 2B, the catheter body 12 comprises a single, central or axial lumen 18. The catheter body 12 is flexible, i.e., bendable, but substantially non-compressible along its length. The catheter body 12 may be of any suitable construction and made of any suitable material. In one embodiment, the catheter body 12 comprises an outer wall 22 made of a polyurethane or PEBAX. The outer wall 22 comprises an imbedded braided mesh of stainless steel or the like to increase torsional stiffness of the catheter body 12 so that, when the control handle 16 is rotated, the tip section of the catheter 10 will rotate in a corresponding manner.

The outer diameter of the catheter body 12 is not critical, but is preferably no more than about 8 French. Likewise the thickness of the outer wall 22 is not critical. The inner surface of the outer wall 22 is lined with a stiffening tube 20, which can be made of any suitable material, preferably polyimide. The stiffening tube 20 is held in place relative to the outer wall 22 at the proximal end of the catheter body 12. A first glue joint 23 is made between the distal ends of the stiffening tube 20 and the outer wall 22 by a fast drying glue, e.g. Super Glue®. Thereafter, a second glue joint 25 is formed between the proximal ends of the stiffening tube 20 and outer wall 22 using a slower drying but stronger glue, e.g., polyurethane.

The stiffening tube 20, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22. Polyimide tubing is suitable because it may be very thin walled while still providing very good stiffness. This maximizes the diameter of the central lumen 18 without sacrificing strength and stiffness. Polyimide material is typically not used for stiffening tubes because of its tendency to kink when bent. However, it has been found that, in combination with an outer wall 22 of polyurethane, PEBAX or other similar material, particularly having a stainless steel braided mesh, the tendency for the polyimide stiffening tube 20 to kink when bent is essentially eliminated with respect to the applications for which the catheter is used.

In one embodiment, the outer wall 22 has an outer diameter of about 0.092 inch and an inner diameter of about 0.063 inch and the polyimide stiffening tube 20 has an outer diameter of about 0.0615 inch and an inner diameter of about 0.052 inch.

Figure 3:
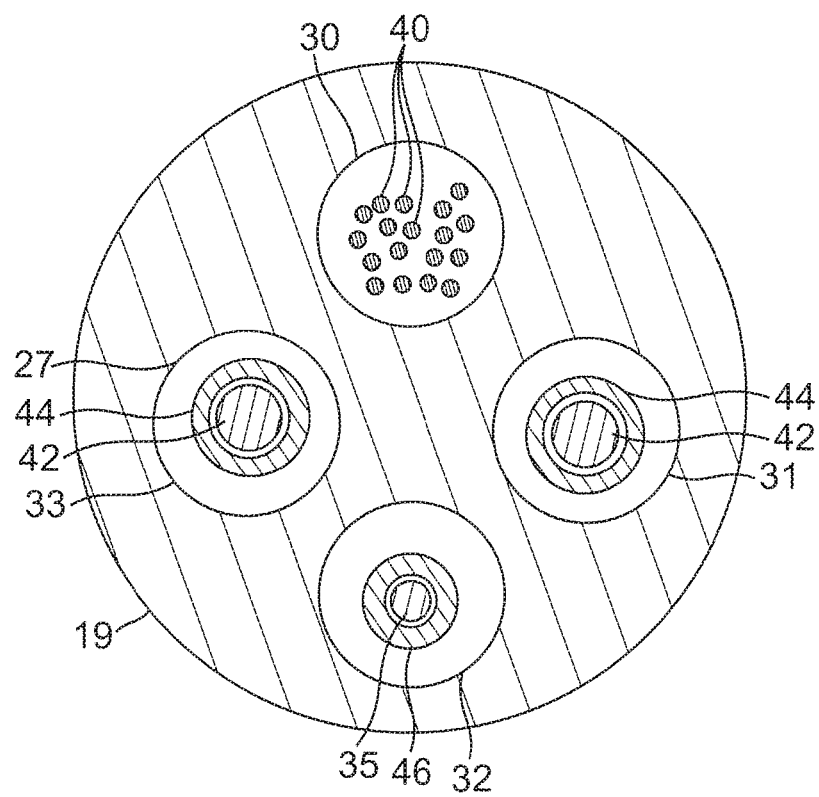
FIG. 3 is an end cross-sectional view of the intermediate section of FIGS. 2A and 2B.

As shown in FIGS. 2A, 2B and 3, the intermediate section 14 comprises a shorter section of tubing 19 with multiple lumens, for example, first, second, third and fourth lumens 30, 31, 32 and 33. The tubing 19 is made of a suitable non-toxic material which is preferably more flexible than the catheter body 12. A suitable material for the tubing 19 is braided polyurethane, i.e., polyurethane with an embedded mesh of braided stainless steel or the like. The outer diameter of the intermediate section 14, like that of the catheter body 12, is preferably no greater than about 8 French. The size of the lumens is not critical. In one embodiment, the intermediate section has an outer diameter of about 7 French (0.092 inch) and the lumens are generally about the same size, having a diameter of about 0.022 inch, or selected lumens can have a slightly larger diameter of about 0.036 inch.

A means for attaching the catheter body 12 to the intermediate section 14 is illustrated in FIGS. 2A and 2B. The proximal end of the intermediate section 14 comprises an inner counter bore 24 that receives the outer surface of the polyimide stiffener 20. The intermediate section 14 and catheter body 12 are attached by glue 29 or the like.

As shown in FIGS. 2A and 2B, extending through the single lumen 18 of the catheter body 12 are various components, for example, lead wires and multiple puller wires, and any other wires or cables. Longitudinal movement of the puller wires relative to the catheter body 12 enables user control of various parts of the catheter via the control handle. As mentioned, in one embodiment, there are first and second deflection puller wires 42 for deflecting the intermediate section 14 and a third puller wire 35 for manipulating and adjusting the distal assembly 17 of the tip section 15.

A single lumen catheter body 12 may be preferred over a multi-lumen body because the single lumen 18 body can permit better tip control when rotating the catheter 10. The single lumen 18 permits the components passing therethrough to float freely within the catheter body. If such components were restricted within multiple lumens, they can build up energy when the handle 16 is rotated, resulting in the catheter body 12 having a tendency to rotate back if, for example, the handle is released, or if bent around a curve, to flip over, either for which are undesirable performance characteristics.

As also shown in FIG. 3, one deflection puller wire 42 extends through the central lumen 18 of the catheter body 12 and into the second lumen 31 of the intermediate section 14. Another deflection puller wire 42 extends through the central lumen 18 and into the fourth lumen 33 of the intermediate section 14. In that regard, the lumens 31, 33 should be off-axis and diametrically opposed to each other for bi-directional deflection in a plane. The distal ends of the deflection puller wires 42 are anchored to the wall of the tubing 19 near the distal end of the intermediate section 14 by means of T-anchors (not shown) as understood by one of ordinary skill in the art. In the intermediate section 14, each deflection puller wires 42 extends through a plastic, e.g. Teflon®, sheath 41, which prevents the deflection puller wires 42 from cutting into the wall of the tubing 19 of the intermediate section 14 when the intermediate section 14 is deflected.

As shown in FIG. 2B, compression coils 44 in surrounding relation to the deflection puller wires 42 extend from the proximal end of the catheter body 12 to the proximal end of the intermediate section 14. The compression coils 44 are made of any suitable metal, e.g., stainless steel. The compression coils 44 are tightly wound on itself to provide flexibility, i.e., bending, but to resist compression. The inner diameter of the compression coils 44 is preferably slightly larger than the diameter of the puller wires 42. For example, when a puller wire 42 has a diameter of about 0.007 inches, the compression coil 44 preferably has an inner diameter of about 0.008 inches. The Teflon® coating on the puller wire 42 allows them to slide freely within the compression coils 44. The outer surface of the compression coils 44 is covered by a flexible, non-conductive sheath 27 to prevent contact between the compression coils 44 and other components, such as lead wires and cables, etc. In one embodiment, a non-conductive sheath is made of polyimide tubing.

The compression coils 44 are anchored at their proximal ends to the proximal end of the stiffening tube 20 in the catheter body 12 by glue joint 51 (FIG. 2B) and at its distal end near the proximal end of the intermediate section 14 in the second lumen 31 and fourth lumen 33 by glue joints 49 (FIG. 2B).

Figure 4:
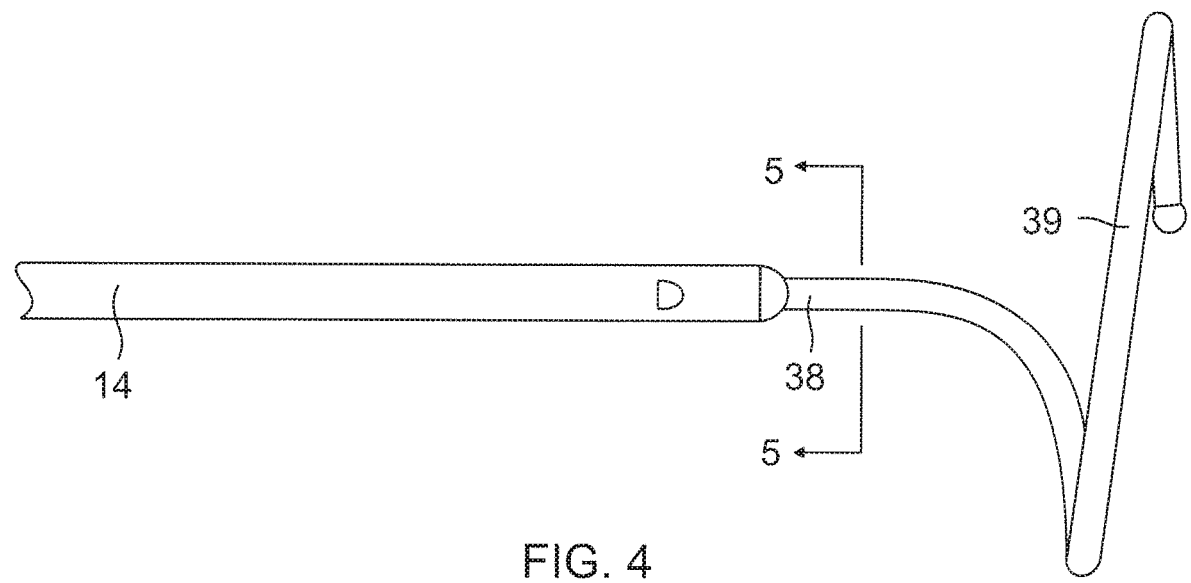
FIG. 4 is a side view of an embodiment of a distal assembly.
Figure 5:
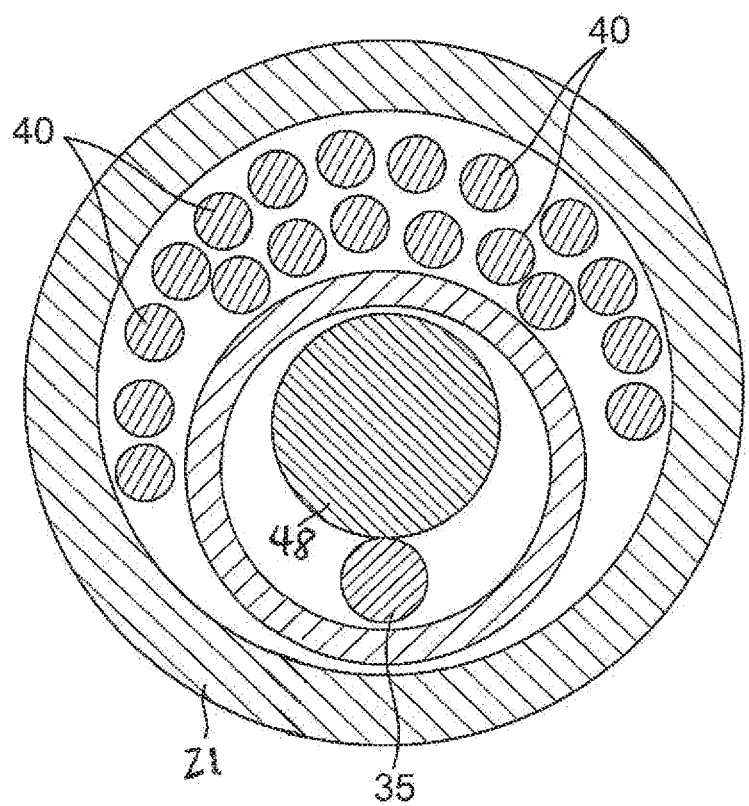
FIG. 5 is an end cross-sectional view of a generally straight proximal portion of the distal assembly of FIG. 4, taken along line 5-5.

With reference to FIG. 4, at the distal end of the intermediate section 14 is the distal assembly 17. The distal assembly 17 comprises a generally straight proximal region 38 and a generally circular main region 39. The proximal region 38 is mounted on the intermediate section 14 and the main region 39 carries a plurality of electrodes for mapping and/or ablation. In the embodiment of FIG. 5, the distal assembly 17 includes a tubing 21. A shape memory member 48 and lead wires 40 for electrodes carried on the distal assembly extend through the lumen of the tubing 21 and into the intermediate section 14 and the catheter body 12.

In the disclosed embodiment, the third or contraction puller wire 35 is provided to contract the generally circular main region 39 to thereby change or reduce its diameter, for example, when mapping or ablating circular or tubular regions of the heart. The contraction wire 35 has a proximal end anchored in the control handle 16 as described further below. The contraction wire 35 extends through the central lumen 18 of the catheter body 12, through the third lumen 32 of the intermediate section 14 (FIG. 3) and into the distal assembly 17 (FIG. 5).

A third compression coil 46 is situated within the catheter body 12 and intermediate section shaft 14 in surrounding relation to the contraction wire 35 (FIG. 2A). The third compression coil 46 extends from the proximal end of the catheter body 12 and to near the distal end of the third lumen 32 of the intermediate section 14. The third compression coil 46 is made of any suitable metal, such as stainless steel, and is tightly wound on itself to provide flexibility, i.e., bending, but to resist compression. The inner diameter of the third compression coil 46 is preferably slightly larger than the diameter of the contraction wire 35. The outer surface of the compression coil 46 is covered by a flexible, non-conductive sheath 27A, e.g., made of polyimide tubing. The third compression coil 46 preferably is formed of a wire having a square or rectangular cross-sectional area, which makes it less compressible than a compression coil formed from a wire having a circular cross-sectional area. As a result, the third compression coil 46 keeps the catheter body 12, and particularly the intermediate section 14, from deflecting when the contraction wire 35 is manipulated to contract the distal assembly 17 as it absorbs more of the compression.

The third compression coil 46 is anchored at its proximal end to the stiffening tube 20 of the catheter body 12 by the proximal glue joint 51 and to the intermediate section 14 by a distal glue joint.

It is understood that glue joints throughout the catheter 10 may comprise polyurethane glue or the like. The glue may be applied by means of a syringe or the like through a hole made in the tubing walls. Such a hole may be formed, for example, by a needle or the like that punctures the tubing walls where the needle is heated sufficiently to form a permanent hole. The glue is then introduced through the hole to wick around the component(s) within the tubing to form a glue joint about the entire circumference of the component(s).

The lead wires 40 attached to the ring electrodes on the distal assembly 17 extend through the first lumen 30 of the intermediate section 14 (FIG. 2A), through the central lumen 18 of the catheter body 12, through the control handle 16, and terminate at their proximal end in a connector (not shown) which is connected to an appropriate monitor or other device for receiving and displaying the information received from the ring electrodes. The portion of the lead wires 40 extending through the central lumen 18 of the catheter body 12, control handle 16 and proximal end of the intermediate section 14 is enclosed within a protective sheath 63, which can be made of any suitable material, preferably polyimide.

An electromagnetic position sensor (not shown) is mounted in or near the distal assembly 17, e.g., in the distal end of the intermediate section 14. A sensor cable extends from the sensor into the lumen 30 of the intermediate section (along with the electrode lead wires 40), into the central lumen 18 of the catheter body 12 and into the control handle where it terminates in a suitable connector (not shown).

Figure 6:
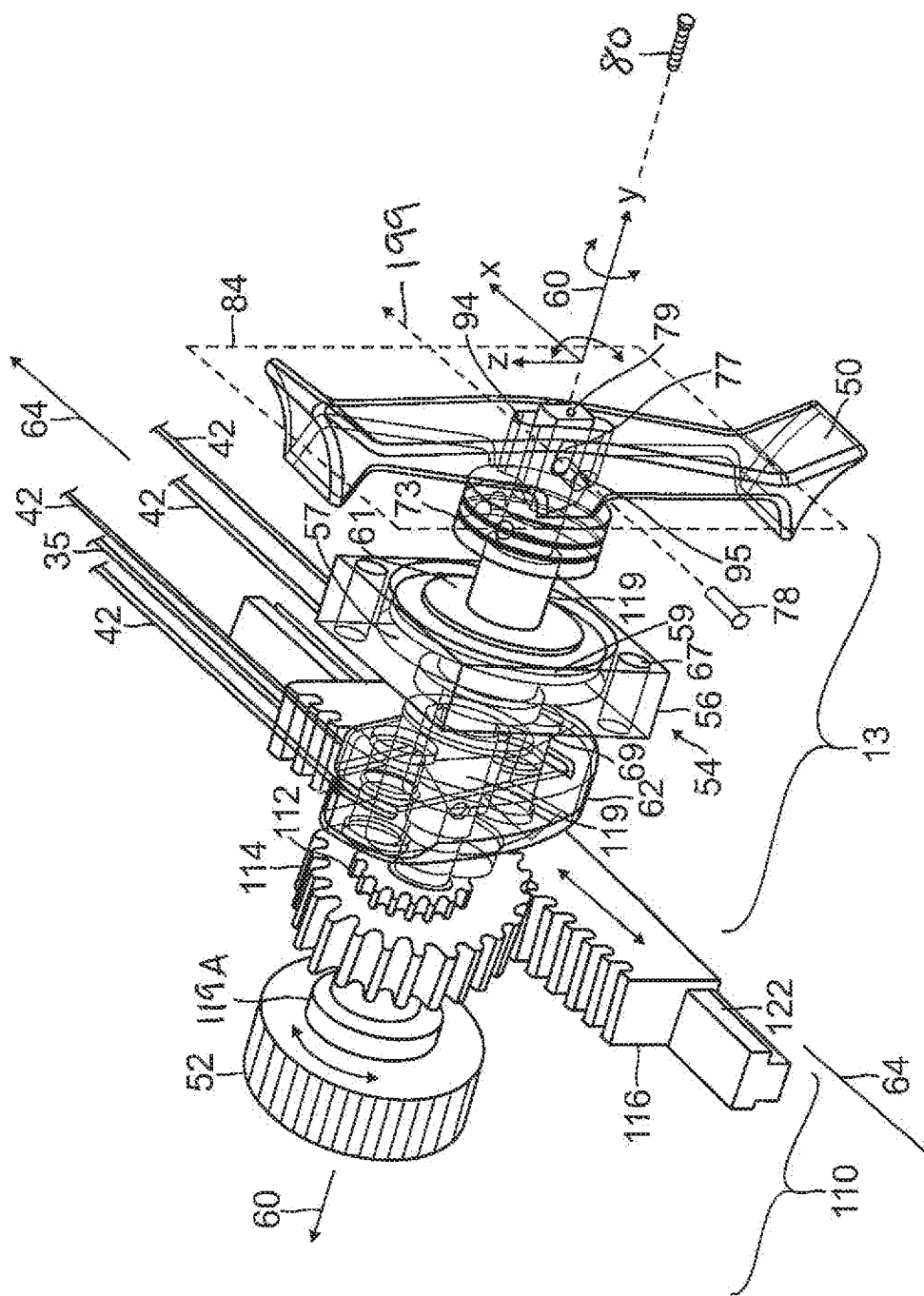
FIG. 6 is a perspective view of the control handle of FIG. 1, showing a first actuation assembly and a second actuation assembly, axially aligned but rotationally independent of each other.
Figure 7A:
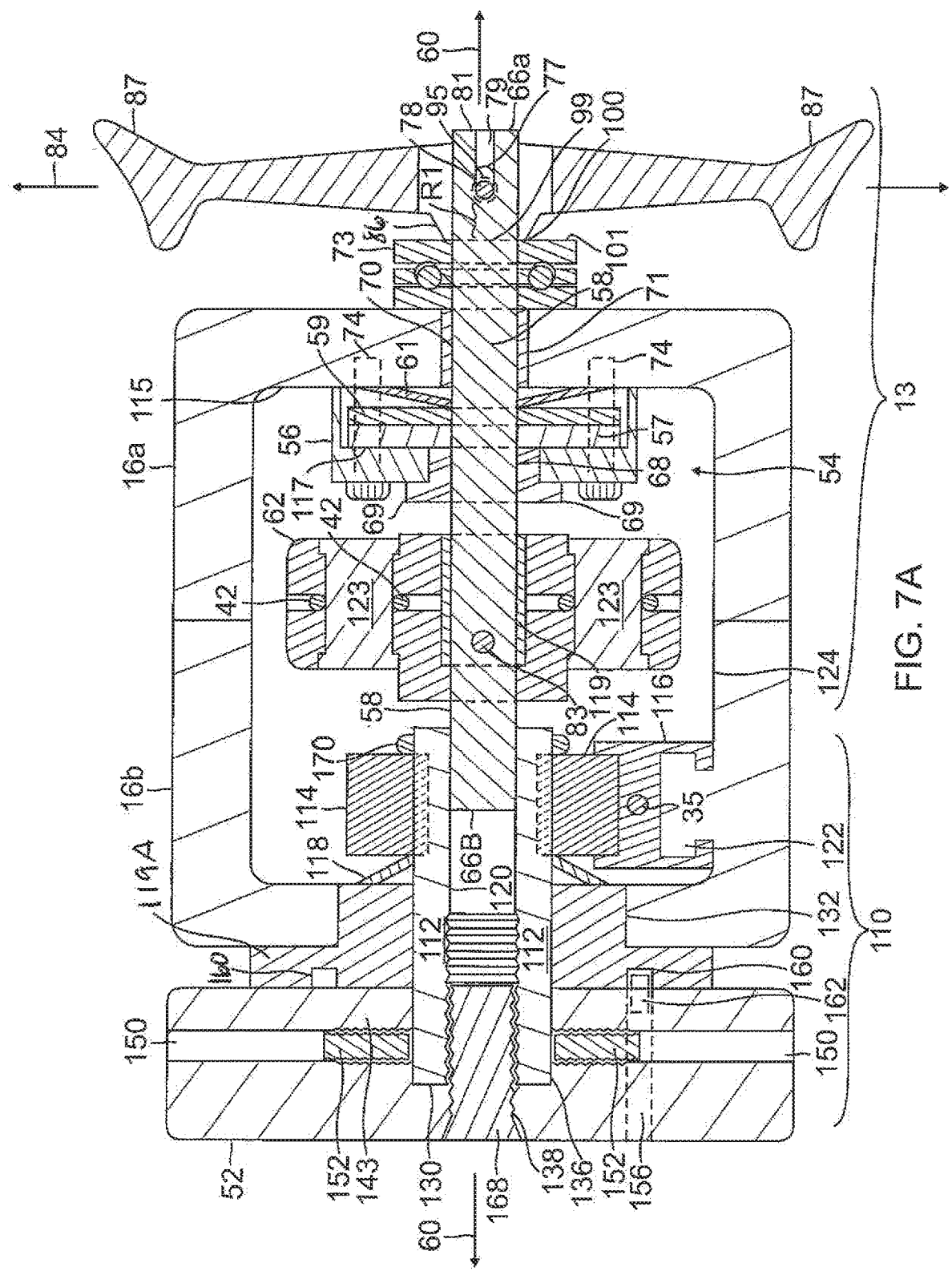
FIG. 7A is an end cross-sectional view of the control handle of FIG. 1, with an engaged clutch mechanism, taken along line 7-7.

In the illustrated embodiment of FIGS. 6 and 7A, the control handle 16 includes a self-holding cam-actuated deflection control assembly 13 which includes the deflection knob 50 for bi-directional deflection of the intermediate section 14 by means of the pair of puller wires 42. Each puller wire 42 is made of any suitable metal, such as stainless steel or Nitinol. Preferably each puller wire has a low friction coating, such as a coating of Teflon® or the like. Each puller wire has a diameter preferably ranging from about 0.006 inch to about 0.012 inch. Preferably both of the puller wires have the same diameter. Flat puller wires may be used in place of round puller wires. Their cross sectional dimensions should be such that they provide comparable tensile strengths as round puller wires.

Alternatively, the puller wires may be replaced in its entirety or in part by tensile fibers. The fibers may be of a high modulus fiber material, preferably having an ultimate tensile strength substantially in the range of 412-463 ksi (2480-3200 Mpa) such as High Molecular Density Polyethylene (e.g., Spectra™ or Dyneema™), a spun para-aramid fiber polymer (e.g., Kevlar™) or a melt spun liquid crystal polymer fiber rope (e.g., Vectran™), or a high strength ceramic fiber (e.g., Nextel™). The term fiber is used herein interchangeably with the term fibers in that the tensile fiber may be of a woven or braided construction. In any case, these materials tend to be flexible, providing suitable durability when used in wrapped engagement with the pulleys and the like for greater throw in deflecting the catheter tip. Further, they are substantially non-stretching, which increases the responsiveness to the manipulation of the control handle, and nonmagnetic so that they generally appear transparent to an MRI. The low density of the material causes it to be generally transparent to an x-ray machine. The materials can also be nonconductive to avoid shorting. Vectran™, for example, has high strength, high abrasion resistance, is an electrical insulator, nonmagnetic, is polymeric, and has low elongation under sustained loading conditions. It is therefore understood that the term "wire" as used herein may be a wire, a tensile fiber, or a tensile member comprising wire segment(s) and tensile fiber segment(s).

As illustrated in FIG. 1, the control handle 16 comprises a generally elongated handle housing, which can be made of any suitable rigid material. The housing can be of a unitary construction or of two opposing halves 16a, 16b that are joined by glue, sonic welding or other suitable means. The deflection control or steering assembly 13 provides bi-directional deflection of the intermediate section 14 in response to manipulations of the knob 50 by a user. The steering assembly defines a generally central rotational axis 60 in relation to its components. The axis 60 is generally perpendicular to a longitudinal axis 64 of the control handle.

Figure 11A:
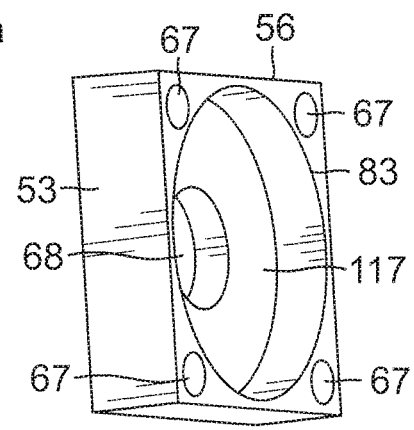
FIG. 11A is a side perspective view of an embodiment of a clutch housing.
Figure 11B:
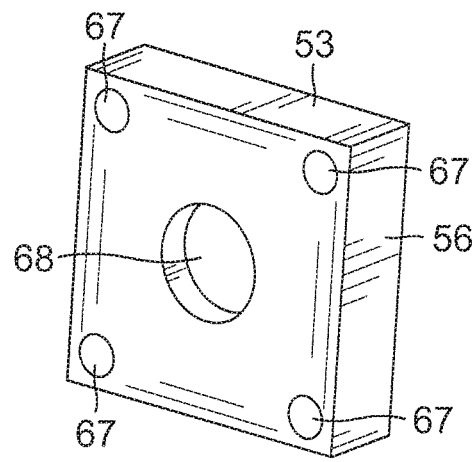
FIG. 11B is another side perspective view of the clutch housing of FIG. 11A.

In the illustrated embodiment, the steering assembly 13 includes the first control knob 50 (FIGS. 8A and 8B) mounted outside of the handle housing 16a, a clutch mechanism 54 inside the control handle 16, a pulley arm 62 (FIGS. 9A and 9B) inside the control handle 16 and a clutch actuation shaft 58 (FIG. 11) that extends transversely through the control handle 16, where the pulley arm 62 and the clutch mechanism 54 are mounted on the shaft 58. The clutch mechanism includes a friction disk 57 that is rotationally coupled to the shaft and a clutch housing 56 (FIGS. 11A and 11B) that provides a friction-inducing surface which generates frictional torque with the friction disk when the two are in contact with each other. The clutch mechanism also includes a support washer 59 for the friction disk 57, and a compression loading washer 61 (FIG. 12) to render the knob 50 self-holding so that deflection set by the user is maintained without the need for the user to continuously hold the knob 50.

In accordance with a feature of the invention, the shaft 58 is adapted for movements in response to forces applied to the knob 50 by the user. In the disclosed embodiment, pivotation of the knob 50 imparts a translational movement in the shaft which disengages the clutch mechanism, and rotation of the knob 50 imparts a rotational movement in the shaft which actuates the puller arm to act on the puller members 42.

Figure 10:
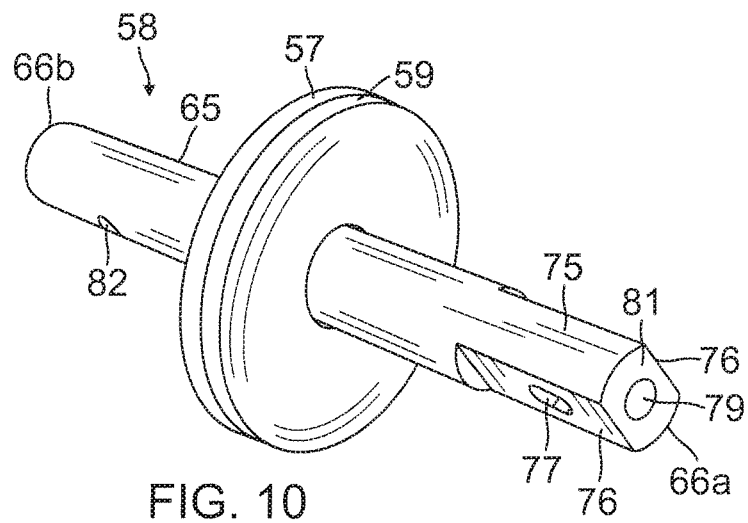
FIG. 10 is a side perspective view of an embodiment of a cam actuation shaft.
Figure 13:
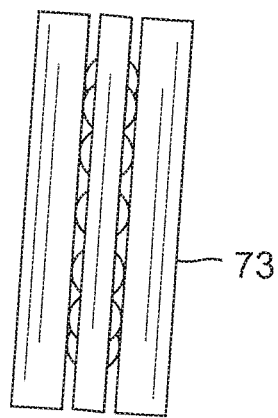
FIG. 13 is a side perspective view of an embodiment of an axial thrust bearing.

In the illustrated embodiment of FIG. 10, the clutch actuation shaft 58 has a generally cylindrical body 65 with two ends 66a, 66b and a predetermined length less than the width of the control handle 16. As shown in FIG. 7A, the first end 66a is supported by the handle housing half 16a as it extends outwardly through a bore 70 in the housing handle half 16a which is lined by a radial bearing sleeve 71. The first end 66a further extends through an axial thrust bearing 73 (FIG. 13) outside of the handle housing half 16a where the knob 50 is mounted on the first end 66a. The knob extends in an x/z plane 84 (FIG. 6) generally perpendicular to the shaft 58 extending along the y axis.

Figure 14:
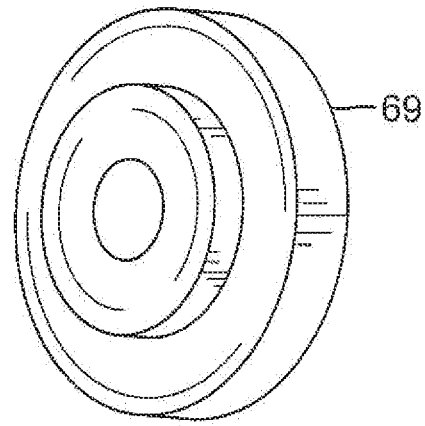
FIG. 14 is a side perspective view of an embodiment of a radial bearing.

Inside the control handle 16 as shown in FIG. 7A, the shaft 58 extends through a center bore 68 of the clutch housing 56 (which is lined by a radial bearing 69 (FIG. 14) that may or may not be a separate component from the clutch housing 56). The second end 66b of the shaft extends toward the opposing housing half 16b. Accordingly, the shaft 58 defines the rotational axis 60 that is perpendicular to the longitudinal axis 64 of the control handle.

As illustrated in the embodiment of FIG. 10, the first end 66a of the shaft 58 on which the knob 50 is mounted has two outer notched portions forming a thinner cross-section 75 with two opposing flat surfaces 76. Extending along the thinner cross-section 75 transversely to the length of the shaft body 65 between the two flat surfaces 76 is a first through-hole 77 for mounting of the knob by means of a pivot pin 78 (FIG. 6). The first through-hole 77 has an elongated or oval cross-section with a longer dimension extending longitudinally along the shaft body 65. In communication with the first through-hole 77 is a partial bore 79 that extends longitudinally between the first through-hole 77 and an adjacent end face 81 of the shaft body. The partial bore 79 receives an adjustment set screw 80 (FIG. 6) for adjusting the position of the pivot pin 78 in the hole 77. The supporting washer 59 (e.g., a brazed washer), is fixed to the shaft body 65 so that it is axially and rotationally fixed to the shaft. Fixed to the washer 59 by adhesive or the like, the friction disk 57 is also axially and rotationally fixed to the shaft 58. The friction disk 57 can be made of any friction-inducing material, e.g., molded sheets of organic or semi-metallic formulations including a matrix of ceramic compounds, mineral fibers and copper fibers that provide friction coefficients ranging from about 0.45-0.55.

Figure 12:
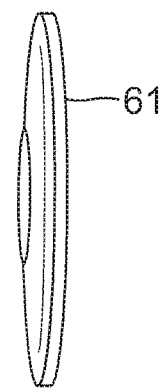
FIG. 12 is a side perspective view of an embodiment of a compression-loading washer.

With reference to FIG. 7A, outwardly of the supporting disk 59 is the compression-loading washer 61, e.g., a Belleville washer (FIG. 12). Immediately inward of the friction disk 57 is the clutch housing 56. In the illustrated embodiment of FIGS. 11A and 11B, the housing 56 has a block body 53 with the center bore 68 that communicates with a larger circular recess 83 that faces the friction disk 57, the support disk 59 and the compression-loading washer 61. Lined with the radial bearing 69, the center bore 68 receives the shaft 58 on which the clutch housing 56 is mounted. The recess 83 however is generally closed to form an interior cavity 113 as the block body 53 has a plurality of bores 67 in a peripheral region surrounding the recess 83 that receive screw fasteners 74 for securing the clutch housing 56 to an interior surface 115 of the control handle housing 16a. The recess 83 is sized with a diameter slightly larger than the generally similar diameter of the friction disk 57, supporting disk 59 and washer 61 to provide clearance for these components. The recess 83 has an axial depth along the y axis that is lesser than a thickness of the clutch housing 56 but greater than a combined thickness of these components so as to provide clearance for the friction disk 57 to be shifted away from contact with an inner surface 117 of the recess 83 along the rotational axis 60 within the confines of the cavity 113 when the clutch is disengaged, as explained further below.

Figure 15:
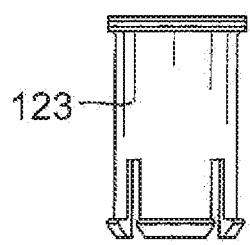
FIG. 15 is a side perspective view of an embodiment of a pulley.
Figure 16:
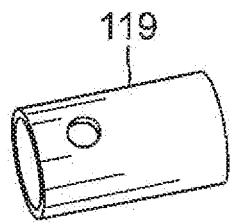
FIG. 16 is a side perspective view of an embodiment of a sleeve bearing.

Further toward the second end 66b of the shaft 58 (FIG. 10) is a through-hole 82 for mounting of the pulley arm 62 by means of a press fit connection pin 83 which axially and rotatably couples the pulley arm 62 to the shaft body 65. A radial bearing 119 (FIG. 16) may line a center bore 121 of the pulley arm 62. A pulley 123 (FIG. 15) occupies a respective through-hole 125 opposing each other across the center bore 121.

As illustrated in FIGS. 17A-17C, the puller wires 42 enter the control handle 16 via a port in the distal end of the control handle. The puller wires enter the pulley arm 62 through a slit opening 127 (FIG. 9B) and each wire is wrapped or wound about a respective pulley 123 about 180 degrees before exiting the pulley arm through the slit opening 127. A proximal end of each puller member 42 is anchored in a stop 147 fixed relative to the control handle 16. By rotating the knob 50 in one direction, the pulley arm 62 is rotated in that direction via the shaft 58 drawing on the puller member 42 on that side to deflect the intermediate section 14 in that direction. A similar pulley arm is described in U.S. Pat. No. 7,377,906, the entire disclosure of which is hereby incorporated by reference.

In accordance with a feature of the invention, friction torque generated between the friction disk 57 and the clutch housing 56 when in contact with each other when the clutch mechanism is engaged serves to render the knob 50 self-holding by resisting rotation of the shaft 58 and the pulley arm 62 fixedly mounted thereon. Thus, rotation of the deflection knob 50 about the rotational axis 60 with the knob remaining within the plane 84 is advantageously resisted by the clutch mechanism 54 when engaged. To disengage the clutch mechanism, the knob 50 is pivoted out of the plane 84, as described further below.

Figure 8B:
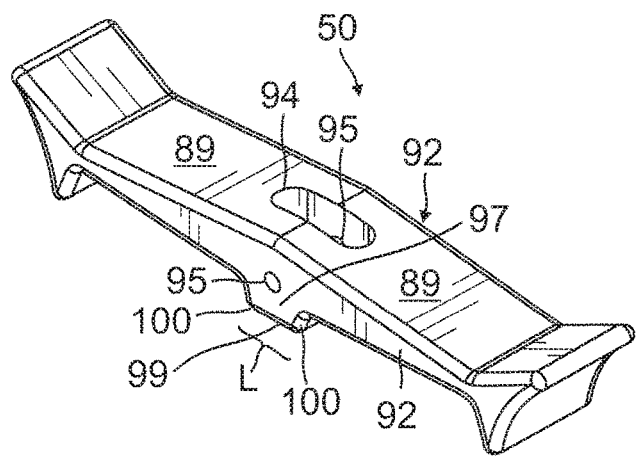
FIG. 8B is another side perspective view of the deflection knob of FIG. 8A.
Figure 8A:
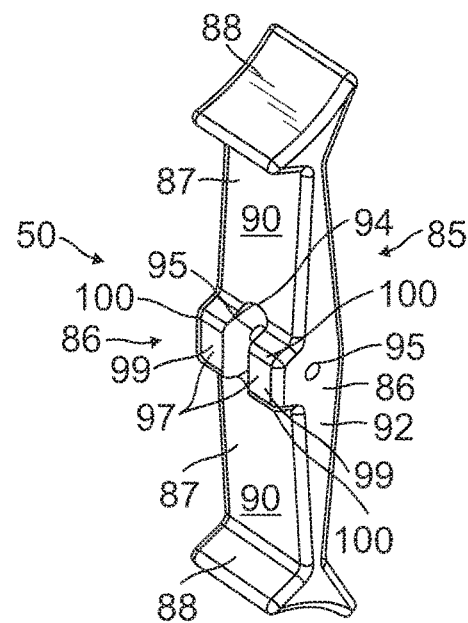
FIG. 8A is a side perspective view of an embodiment of a first actuation member, e.g., a deflection knob.
Figure 9A:
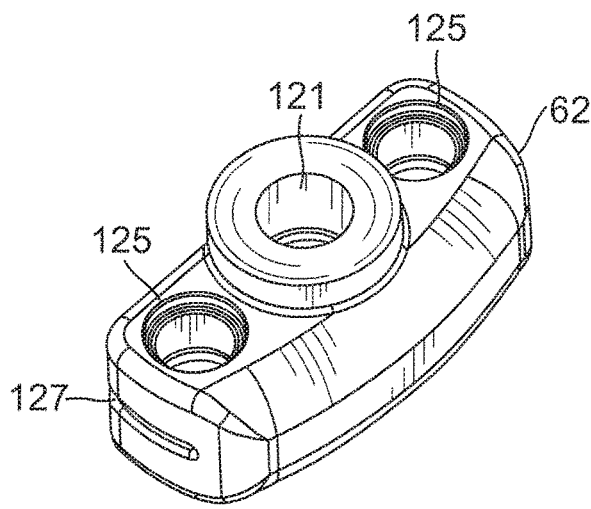
FIG. 9A is a top perspective view of an embodiment of a pulley arm.
Figure 9B:
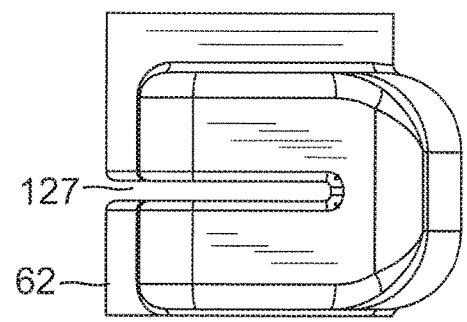
FIG. 9B is an end perspective view of the pulley arm of FIG. 9A.

In the illustrated embodiment of FIGS. 8A and 8B, the knob 50 has an elongated body 85 with two central cam portions 86, two end portions 87 with enlarged ends 88, an outer-facing surface 89, an inner-facing surface 90 and two side surfaces 92. The body 85 is mounted at the central cam portion 86 on the first end 66a of the shaft 58 and positioned perpendicularly to the shaft such that the elongated body 85 defines the plane 84 (FIG. 6). The enlarged ends 88 are adapted for knob 50 manipulations by the user's thumbs and fingers, including (1) pivoting the knob 50 "out-of-plane" to release the clutch mechanism 54 and (2) radially rotating the knob 50 while "out of plane" to rotate the pulley arm 62 for bi-directional deflection of the catheter.

The pivoting manipulation of the knob 50 involves the two central cam portions 86 of the knob 50. Between the central cam portions is a through-opening 94 extending between the outer-facing and inner facing surfaces 89, 90 that receives the first end 66a of the shaft 58. As better seen in FIG. 6, aligned with the oval through-opening 77 of the shaft 58 is a smaller and circular through hole 95 extending through side surfaces 92 of the knob 50 for receiving the pivot pin 78 in providing a pivoting axis 199 for the knob 50 to pivot in and out of the plane 84.

Notably, the through-opening 94 receiving the first end 66*a* of the shaft 58 is substantially enlarged relative to the first end 66*a* so that the end 66*a* has room to maneuver in the through-hole 94 as the knob 50 is pivoted out of the plane 84 to release the clutch mechanism 54. The set screw 80 in the partial axial bore 79 is used to adjust the lateral position of the pivot pin 78 in the through-hole 77 for adjusting the amount of pivot play in the knob 50.

As best seen in FIG. 8A, each central cam portion 86 of the knob is formed with cam lobe 97 projecting from the inner-facing surface 90. Each cam lobe 97 has a generally flat contact surface 99 with a length L that is slightly greater than the diameter of the shaft 58, and two curved contact surfaces or "rounded corners" 100 on opposite sides of the flat contact surface 99. These corners 100 advantageously differ from the flat contact surfaces 99 in terms of their distance to the through-hole 77 and/or pivot pin 78 about which the knob 50 pivots. Thus, pivoting the knob 50 out of the plane 84 changes the engagement of the cam lobes 97 against an outer surface 101 of the axial thrust bearing 73 from the flat surface 99 to either of the corners 100. This change in cam engagement translates the shaft 58 axially relative to the control housing for disengaging the clutch mechanism, as explained below in further detail.

Figure 7B:
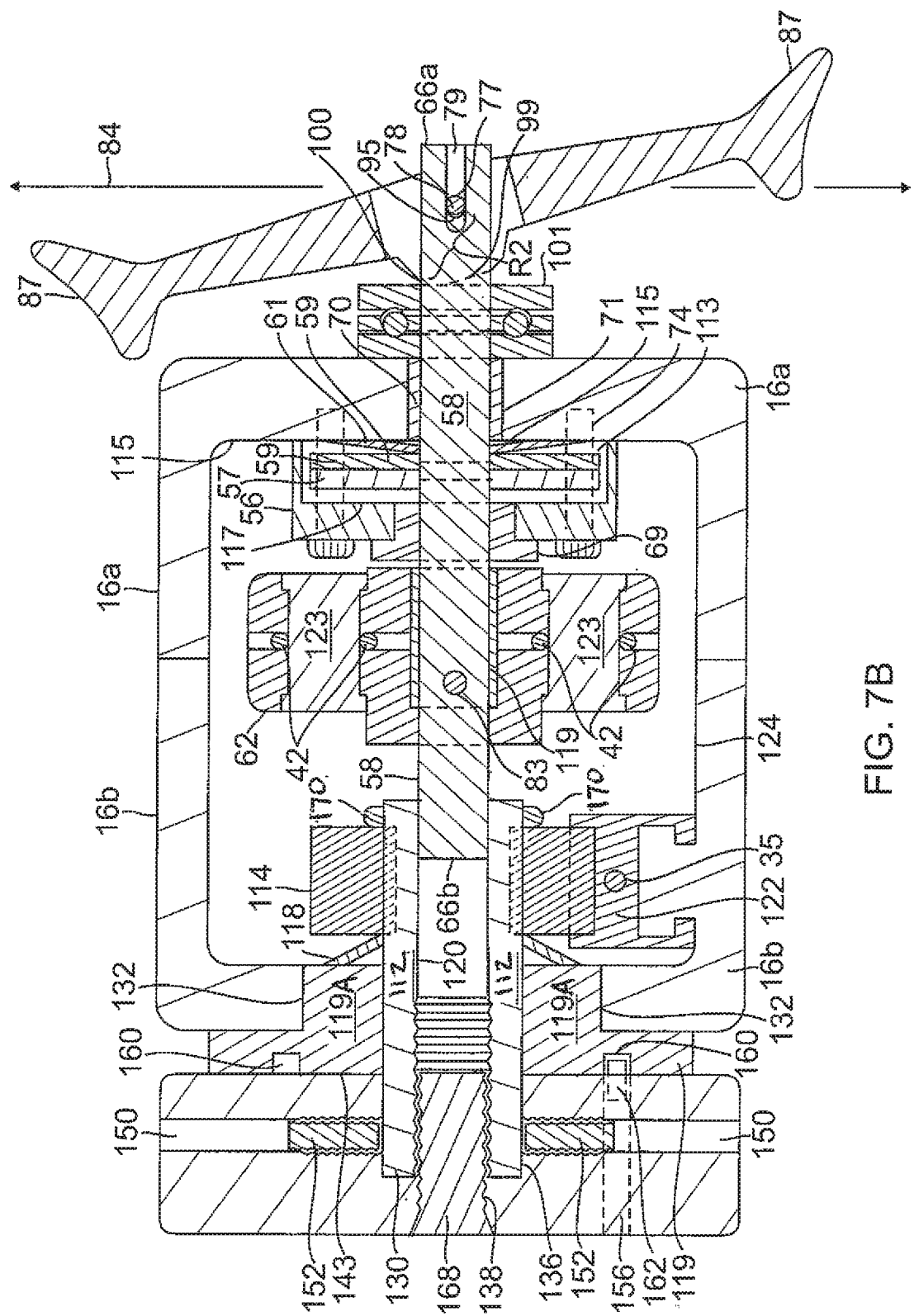
FIG. 7B is an end cross-sectional view of the control handle of FIG. 7A, with a disengaged clutch mechanism.

With reference to FIGS. 7A and 7B, the clutch mechanism 54 includes the housing 56, the friction disk 57, the supporting washer 59 and the compression-loading disk 61, each of which is mounted on the shaft 58 and axially and rotationally coupled thereto. Leveraging against an inner surface 115 of the housing half 16*a*, the compression loading disk 61 preloads the friction disk 57 by compressing it against the inner surface 117 of the recess 83 of the clutch housing 56 in generating frictional torque against rotation of the shaft 58. Thus, with the deflection knob 50 "in plane" (FIG. 7A), the knob resists rotation and advantageously remains in any radial position within the x/z plane 84 as set by user for a desired deflection of the catheter until the clutch mechanism 54 is disengaged by the user.

To disengage the clutch mechanism 54, the user pivots the knob 50 out of the plane 84 by pressing inwardly on either of the two enlarged end portions 87 (FIG. 7B). As the knob 50 is pivoted in this manner, the cam engagement surfaces against the outer surface 101 of the axial thrust bearing 73 change from the flat surfaces 99 of the cam lobes 97 to upper or lower set of cam corners 100 that is closer to the enlarged end portion 87 depressed by the user. This change increases the separation distance between the engagement surface on the axial thrust bearing 73 and the pivot axis 96 (FIG. 6) from distance R1 to distance R2 which moves the pivot pin 78/pivot axis 96 outwardly and causes the shaft 58 to translate outwardly. Because the fiction disk 57 (along with the supporting washer 59 and the compression-loading washer 61) of the clutch mechanism 54 is fixed on shaft 58, the friction disk 57 is also translated outwardly and moved out of frictional contact with the recess surface 117 of the clutch housing 56. As such, the clutch mechanism 54 is disengaged leaving the shaft 58 free to be rotated by the user via the knob 50. Thus, rotation of the knob 50 is facilitated by disengagement of the clutch mechanism only when the knob 50 is pivoted out of the plane 84.

It is understood that the axial thrust bearing can be an integral part of the handle half 16*a*. For exampled, where the control housing is constructed of 30% glass filled polycarbonate material, it may include about 10-15% Teflon® by volume to reduce the static and dynamic contact friction between the cam lobes 97 and the outer handle housing surface during rotation of the knob 50. Moreover, the ball bearing type axial thrust bearing can be replaced by a less costly metal washer located between the cam lobes 97 and the outer handle housing surface (to reduce handle surface wear) where the handle housing is injection molded from a polymer formulation with friction modifiers added (e.g., teflon, silicone and or carbon fibers) to provide uniform non stick-slip actuation of the knob 50 during actuation.

Because the compression-loading washer 61 is compressed against the control handle housing half 16*a* while the clutch mechanism 54 is disengaged, the clutch mechanism is biased by the compression-loading washer 61 toward re-engagement. That is, once the user releases pivotation of the knob 50, the compression-loading washer 61 springs back to its original shape thereby automatically translating the shaft 58 inwardly and pushing the friction disk 57 back into frictional contact with the recess surface 117. The translation pulls the knob 50 back into the plane 84 (FIG. 7A) where the cam engagement surfaces with the axial thrust bearing 73 return to the flat surfaces 99. Once again, the clutch mechanism 54 is engaged and the knob 50 resists rotation.

Because of the repeated cycles of bending each deflection puller wire 42 can experience around its pulley 123, the segment of each puller wire within the control handle, and especially around the pulleys, may comprise a tensile fiber segment such as described hereinabove, which can better withstand stress and strain. To that end, a crimped connector 129 (FIGS. 17A-17C) is provided to connect a proximal end of each first and second distal puller wire segments 42D to a distal end of a respective proximal tensile fiber segment 42P.

Figure 19:
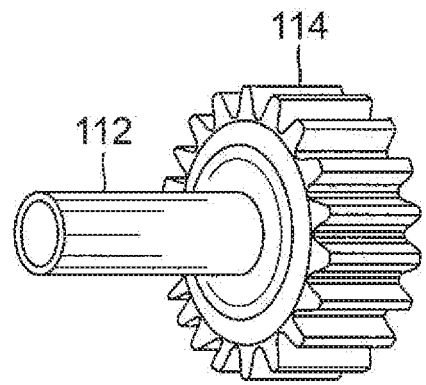
FIG. 19 is a side perspective view of an alternate embodiment of a partially splined shaft.

With reference to FIGS. 6 and 7A, housed generally in the other housing half 16*b* is a second puller wire actuation assembly 110 which includes a shaft 112 with a partial outer spline, a spur gear 114 rotationally coupled to the shaft 112 by means of an inner spline interlocking with the outer spline, a translating member 116 responsive to rotation of the shaft 112, a compression-loading washer 118 and the actuation dial 52. It is understood that the spur gear 114 can be formed as a spur gear formation integral with the splined shaft 112 as a single component, as illustrated in FIG. 19. The spur gear-shaft combination may be a single piece injection molded design to reduce production costs. The shaft and gear may be made from injection molded powdered metal or the shaft can be metal (e.g., brass alloy 260 or stainless steel) and the plastic spur gear can be insert molded onto the metal shaft. The shaft 112 has a longitudinal bore 120. At an inner end, the bore receives the second end 66*b* of the clutch actuation shaft 58 of the first actuation assembly 13. The second end 66*b* is sized slightly smaller in diameter relative to the bore 120 so that the shafts 58 and 112 can rotate independently of each other and the second end 66*b* can translate away from the shaft 112 as needed. Thus, there is no strict rotational coupling between the shaft 58 of the first actuation assembly and the shaft 112 of the second actuation assembly although they are axially aligned.

In the disclosed embodiment, the translating member is a rack 116 positioned below the spur gear 114 (or spur gear formation, used interchangeably herein) in engagement therewith such that rotation of the spur gear 114 imparts to the rack 116 a translational movement (arrow 131) in the longitudinal direction 64 of the control handle 16. The rack 116 sits on a raised ridge or track 122 formed in an inner surface 124 of the control handle housing half 16*b*. The track 122 guides the movement of the rack 116 along the longitudinal direction. It is understood that rotation of the dial 52 in one direction results in the rack translating distally and rotation in the opposite direction results in the rack translating proximally. A proximal end of the third puller member 35 is anchored in the rack 116 so that the translational motion of the rack actuates the third puller member in manipulating another feature of the catheter, for example, tightening the helical form of the distal assembly.

As best shown in FIG. 7A, the actuation dial 52 is mounted on an outer end 130 of the shaft 112 which extends through a through-hole 132 in the control handle housing half 16b. The through-hole 132 is lined with a radial bearing 119A (FIGS. 18A and 18B) which can be integrally molded as part of the housing half 16b. In that regard, either or both of the housing halves can be constructed of a plastic material with fiberglass, for example, approximately 30% fiberglass by volume, to minimize risk of permanent deformation under long term loading conditions when the various washers are compressed. The bearing 119A can be a sintered metal sleeve bearing to prevent permanent deformation or "creep" of the handle housing under long term compression loading.

Figure 18A:
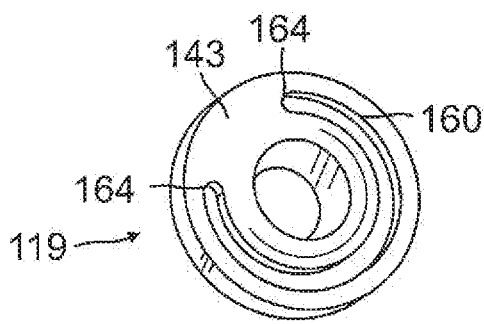
FIG. 18A is a side perspective view of an embodiment of a radial bearing with an outer surface formed with a rotation track.
Figure 18B:
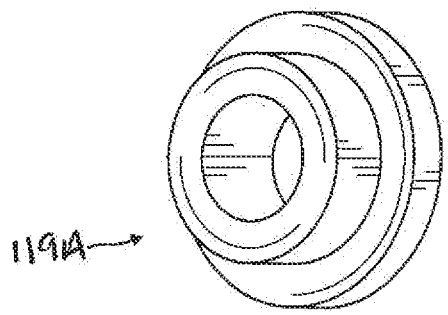
FIG. 18B is a side perspective view of an inner surface of the radial bearing of FIG. 18A.
Figure 20:
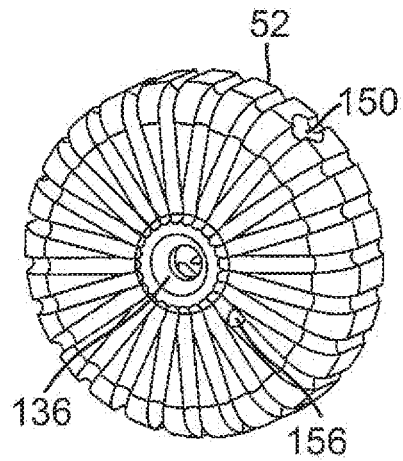
FIG. 20 is a side perspective view of an embodiment of a second actuation member, e.g. a contraction wire dial.

In the illustrated embodiment of FIG. 20, the actuation dial 52 has a disk shape with a circular cross-section. The outer end 130 of the shaft 112 is received in a central partial bore 136 in the actuation dial 52. In communication with the central partial bore 136 of the dial 52 are two opposing radially transverse bores 150. A set screw 152 is inserted in each bore 150 for frictional contact with the shaft 112 in rotationally coupling the dial 52 and the shaft 112. An off-center through-bore 156 parallel with the shaft 112 is formed in the actuation dial 52. The bore 156 is in communication with a C-shaped groove 160 formed in an outer-facing surface 143 of the bearing 119A (FIG. 18A). A press-fit pin 162 is inserted into the bore 156 with its end received and riding in the groove 160. Ends 164 of the groove act as stops for the pin 162 in limiting the degree of rotational movement of the dial 52 in setting a maximum and minimum travel of the third puller wire 35 for adjusting the distal assembly 17. It is understood that the groove 160 can be integrally molded as part of the control handle housing half 16b.

A second locking cap screw 168 secures the dial 52 to the shaft 112. The cap screw 168 also provides incremental friction adjustment means to render the dial 52 self-holding by allowing adjustment of the axial compression of the components on the shaft 112, especially the compression loading washer 118. The screw 168 is received a center bore 138 of the dial 52 in communication and axially aligned with the larger bore 136. The screw 168 engages the shaft 112 through the bore 120 therein. A retaining ring 170 (FIG. 7A) mounted on the shaft 112 secures the shaft 112 against the spur gear 114. The retaining ring 170 secures the second assembly in place and also preloads the compression washer 118 against the bearing 119A to render the dial 52 self-holding.

In use, a suitable guiding sheath is inserted into the patient with its distal end positioned at a desired location. An example of a suitable guiding sheath for use in connection with the present invention is the Preface™. Braiding Guiding Sheath, commercially available from Biosense Webster, Inc. (Diamond Bar, Calif.). The distal end of the sheath is guided into one of the chamber, for example, the atria. A catheter in accordance with an embodiment of the present invention is fed through the guiding sheath until its distal end extends out of the distal end of the guiding sheath. As the catheter is fed through the guiding sheath, the distal assembly 17 is straightened to fit through the sheath. Once the distal end of the catheter is positioned at the desired location, the guiding sheath is pulled proximally, allowing the deflectable intermediate section 14 and distal assembly 17 to extend outside the sheath, and the distal assembly 17 returns to its original shape due to its shape-memory.

With the deflection knob 50 "in plane", the clutch mechanism is engaged so that the deflection knob 50 resists rotation. However, by pivoting the deflection knob 50 "out of plane", the user disengages the clutch mechanism 54 so that the knob 50 can be rotated to actuate the pulley arm 62 for deflecting the intermediate section 14. Turning the deflection knob 50 in one direction deflects the intermediate section 14 to that direction. Turning the deflection 50 in the opposite direction deflects the intermediate section 14 to that opposite direction. When the desired deflection has been achieved, the user releases the knob 50 which readily returns to "in plane" with the clutch mechanism being re-engaged to render the knob self-holding.

The user may then adjust the generally circular main region 39 of the distal assembly 17 by rotating the dial 52 in one direction to tighten and decrease the generally circular main region or in the opposite direction to loosen and increase. By manipulating the dial 52, the generally circular main region 39, is adjusted to fit the pulmonary vein or other tubular structure. In the disclosed embodiment, by rotating the dial in one direction, the contraction wire 35 is drawn proximally to tighten and decrease the diameter of the generally circular region 39 and by rotating the dial in the other direction, the third puller or contraction wire 35 is loosened to release the generally circular region 39 to its original diameter. Preferably at least about 50%, more preferably at least about 70%, and still more preferably at least about 80% of the circumference of the generally circular main region is in contact with a circumference inside the tubular region. When the desired circumference has been achieved, the user releases the dial 52 which is also self-holding. The circular arrangement of the electrodes on the generally circular portion 39 permits measurement of the electrical activity at that circumference of the tubular structure so that ectopic beats between the electrodes can be identified. The size of the generally circular main region 39 permits measurement of electrical activity along a diameter of a pulmonary vein or other tubular structure of or near the heart because the circular main region has a diameter generally corresponding to that of a pulmonary vein or other tubular structure. Because the shafts 58 and 112 are not rotationally coupled, each shaft can be rotate independently of the other and hence each actuation assembly can function independently of the other.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. For example, the catheter can be adapted such that the third puller wire advances and retracts another component such as a guide wire or a needle. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A control handle for a medical device having at least first and second features and at least first and second puller members for manipulating the first and second features, the control handle comprising:
   a housing having a longitudinal axis;
   a first actuation assembly comprising:
      a first shaft having a length defining a first rotational axis generally perpendicular to the longitudinal axis,
      a first actuator mounted on the first shaft and extending in a plane generally perpendicular to the first shaft, the first actuator being pivotable about a pivot axis oriented generally parallel to the longitudinal axis; and
      a pulley arm mounted on and coupled to the first shaft, the pulley arm adapted to translate the first puller member upon rotation of the first shaft; and
   a second actuation assembly having a second rotational axis, the second actuation assembly comprising:
      a second actuator;
      a second shaft rotationally coupled to the second actuator, the second shaft defining the second rotational axis;
      a spur gear formation on the second shaft; and
      a rack responsive to the spur gear formation for translational movement in response to rotation of the spur gear formation, wherein a proximal end of the second puller member is anchored in the rack.

2. The control handle of claim 1, wherein the first actuator has a cam portion providing a first engagement surface and a second engagement surface, the first engagement surface being actuated when the first actuator is in the plane and the second engagement surface being actuated when the first actuator is out of the plane.

3. The control handle of claim 2, wherein the first engagement surface is generally flat and the second engagement surface is curved.

4. A control handle of claim 3, wherein a first separation distance between the first engagement surface and the pivot axis is lesser than a second separation distance between the second engagement surface and the pivot axis.

5. The control handle of claim 4, wherein the first shaft is adapted for translation along its length between a first position and a second position in response to pivotation of the first actuator.

6. The control handle of claim 1, wherein the first shaft has an outer end and the first actuator has an enlarged through-hole that receives the outer end on which the first actuator is pivotally mounted.

7. A catheter adapted for mapping and/or ablation, comprising
   an elongate catheter body;
   an intermediate deflectable section disposed distal to the catheter body;
   a distal assembly disposed distal to the intermediate deflectable section;
   a control handle disposed proximal to the catheter body, the control handle comprising a housing including a longitudinal axis, a first actuation assembly, and a second actuation assembly; and
   at least a first puller member extending between the control handle and the intermediate deflectable section and a second puller member extending between the control handle and the distal assembly;
   the first actuation assembly comprising:
      a first shaft having a length defining a first rotational axis generally perpendicular to the longitudinal axis,
      a first actuator mounted on the first shaft and extending in a plane oriented generally perpendicular to the first shaft, the first actuator being pivotable about a pivot axis generally parallel to the longitudinal axis, and
      a pulley arm mounted on and coupled to the first shaft, the pulley arm adapted to translate the first puller member upon rotation of the shaft; and
   the second actuation assembly comprising:
      a second actuator;
      a second shaft rotationally coupled to the second actuator;
      a spur gear formation on the second shaft; and
      a rack responsive to the spur gear formation for translational movement in response to rotation of the spur gear formation, wherein a proximal end of the second puller member is anchored in the rack.

8. The catheter of claim 7, wherein the first actuator has a cam portion providing a first engagement surface and a second engagement surface, the first engagement surface being actuated when the first actuator is in the plane and the second engagement surface being actuated when the first actuator is out of the plane.

9. The catheter of claim 8, wherein the first engagement surface is generally flat and the second engagement surface is curved.

10. The catheter of claim 7, wherein the first actuator is pivotable about a pivot axis and a first separation distance between the first engagement surface and the pivot axis is lesser than a second separation distance between the second engagement surface and the pivot axis.

11. The catheter of claim 8, wherein the shaft is adapted for translation along its length between a first position and a second position in response to pivotation of the first actuator.

* * * * *